United States Patent [19]

McRae

[11] Patent Number: 5,036,709

[45] Date of Patent: Aug. 6, 1991

[54] PAVING MATERIALS TESTING MACHINE

[76] Inventor: John L. McRae, P.O. Box 1109, Vicksburg, Miss. 39180

[21] Appl. No.: 538,667

[22] Filed: Jun. 15, 1990

Related U.S. Application Data

[62] Division of Ser. No. 362,283, Jun. 6, 1989, Pat. No. 4,942,768.

[51] Int. Cl.$^5$ .............................................. G01N 3/24
[52] U.S. Cl. ..................................................... 73/841
[58] Field of Search ................ 73/794, 795, 806, 807, 73/808, 811, 813, 815, 816, 818, 841, 789, 842, 843, 845

[56]     References Cited

U.S. PATENT DOCUMENTS

| | | | |
|---|---|---|---|
| 2,972,249 | 2/1961 | McRae et al. | 73/794 |
| 3,127,765 | 4/1964 | O'Neil | 73/813 |
| 3,478,572 | 11/1969 | McRae et al. | 73/825 |
| 3,618,369 | 11/1971 | Hamilton et al. | 73/808 |

Primary Examiner—Robert Raevis
Attorney, Agent, or Firm—Berman, Aisenberg & Platt

[57]     ABSTRACT

An electronically instrumented combination kneader compactor and plane-strain, simple-shear testing machine for use in testing paving materials under cyclic loading and over a range of temperatures and various rates of shear has been described. A very significant advance in pavement materials testing is made available in the machine by introducing cyclic vertical loading simultaneously with kneading shear—this being analogous to what actually happens in the pavement beneath a moving vehicle tire. Fundamental engineering (stress-strain) measurements, including dynamic moduli, are obtained which are suitable for use in design calculations in a rational engineering approach to flexible payment design in lieu of the conventional empirical correlations. The optimum bitumen or water content is precisely determined on the basis of the elasto-plastic properties response and independently of conventional empirical correlations with the percentage of voids. The amount and rate of compaction in terms of mass per unit volume per cycle of pavement design load applications is measured and conveniently displayed so as to indicate the ultimate compaction for a given pavement design stress. This is the unit weight (density) required by the engineering specifications to insure against rutting caused by further compaction under traffic.

4 Claims, 4 Drawing Sheets

FIG_5

PAVING MATERIALS TESTING MACHINE

This is a division of U.S. application 07/362,283 which was filed on June 6, 1989, now U.S. Pat. No. 4,942,768.

TECHNICAL FIELD

This invention relates to the art of apparatus for testing samples of granular plastic paving materials such as gravel, stone or soil, which are mixed with water or bitumen and include additives such as lime or cement and various other chemicals and compounds used to enhance the paving mixture or paving foundation material.

BACKGROUND ART

In addition to some measure of conventional shear strength, a desirable feature for testing devices for materials for flexible pavements, is to be able to indicate the optimum bitumen content or water content along with the optimum unit weight (density), as well as the shear strength and the dynamic moduli of the compacted test specimen when subjected to cyclic loading. The optimum bitumen content for current paving materials design tests, employing a fixed compaction effort, are largely based upon empirical correlations with limited ranges of voids, i.e. empirical voids criteria. This approach is not universally applicable because the void content is a variable and different criteria are needed when the material changes or the compaction effort changes. Some paving materials design tests employ tamping as the compaction method where the number of tamps of a given magnitude (impact of kneading) are empirically correlated with the unit weight (density) developed under traffic, and these become obsolete when the traffic loads change.

Other machines for testing paving materials by kneading under pressure are known. In U.S. Pat. Nos. 2,972,249 and 3,478,572 shear strain and unit weight (density) are tested by a kneader compactor which is essentially a mechanical analog of the pavement structure which permits adjusting the design stress in accord with the anticipated pavement design loading. In U.S. Pat. No. 3,478,572, a device for measuring wall friction of the sample with respect to the mold is also provided.

In machines of this type, a mold chuck receives a cylindrical mold containing a sample of material such as gravel, stone or soil, usually mixed with bitumen or water. The sample is subjected to a controlled compressive load by a hydraulic ram and to controlled shear strain by a oscillator mechanism which applies a gyratory motion to the chuck into which the mold is clamped. The gyratory angle response is a measure of shear strain under the applied loading and is thus an indication of the plastic properties of the sample. As the sample is kneaded and compacted the gyration varies in response to changes in the physical properties of the sample and the point at which it starts to progressively increase with continue kneading is significant in that it indicates a critical degree of saturation (percentage of voids filled) in the densification process.

Other machines used previously for measuring the dynamic moduli (compression and rebound) under cyclic loading have simply employed cyclic loading on a confined or unconfined cylinder of the paving material—the cylinder receiving no added distortional stress in conjunction with the cyclic vertical stress. This is not analogous to the action occurring in the pavement layer beneath a moving wheel as the pavement layer actually deflects under the load thus introducing a combined action of internal particle movement or so-called kneading action in conjunction with the vertical compression under the wheel load and rebound with the passage of the wheel load.

The prior art does not provide a machine that will measure the required design parameters and furnish information displays that permit automatic, convenient and positive determination of the relevant parameter of optimum bitumen content or water content along with the relevant unit weight (density) and dynamic moduli and strength properties under dynamic conditions for use in designing flexible type pavement.

SUMMARY OF THE INVENTION

In accordance with the invention, a testing machine conveniently defines a critical condition in terms of the unit weight (density) of the sample at which excess plasticity begins to occur when being subjected to kneading action under the anticipated design stress. This definition is in lieu of an empirical correlation between the actual pavement and given laboratory compaction effort defined in terms of a given number of cycles of kneading. Obviously, the optimum bitumen or water content must be less than that at which this excess plasticity occurs, but not so much less as to cause unfavorable qualities associated with deficient plasticity, resulting in excess porosity accompanied by cracking, and raveling. Additionally, the unit weight (density) at the selected optimum must be sufficient to preclude further densification under traffic, resulting in ruts due to compaction under traffic.

Cyclic vertical loading is combined with a kneading action to simulate the action and reaction in the pavement structure more accurately.

The unit weight (density) and number of gyrations of the kneading compaction load are recorded and digitized. A predetermined slope of a graph representing these parameters is identified at a point approximating the asymptotic condition, i.e. essentially a fully compacted condition, under the anticipated pavement design loading. At the same time, the machine produces a record of the shear strain (gyratory shear angle) which indicates precisely when the test specimen becomes excessively plastic, indicating the limiting allowable quantity of bitumen or water, as the case may be. The shear resistance is also measured and recorded while the shear strain and density are being measured. Upon completion of the compaction, the specimen is subjected to cyclic vertical loading while experiencing a kneading action simulating the kneading that occurs in the pavement caused by actual traffic loads. Thus, the invention provides an engineer with a tool which identifies the optimum condition for any given traffic loading for a given material and simultaneously measures the unit weight (density) and the shear strength as well as the dynamic moduli for the compacted test specimen while being subjected to a kneading action simulating the action on the actual pavement under traffic.

An object of this invention is to provide a materials testing machine that provides a mechanical analog of a unit of flexible pavement and which measures significant pavement design parameters of a flexible pavement specimen, such as optimum bitumen or water content, optimum unit weight (density) and plane-strain, simpleshear properties including dynamic moduli (under cyclic loading) suitable for theoretically sound design calculations.

Another object of this invention is to automatically indicate when a test specimen begins to show a progressive flattening of the stress-strain curve with continued densification (simulating compaction in the actual pavement) under the anticipated pavement design stress.

Yet another object of this invention is to provide means for conveniently identifying the unit weight (density) at which the rate of densification (density change vs cycles of kneading) has reached a prescribed value (for example, one pound per cubic foot per 100 revolutions) when employing the anticipating pavement design stress.

Still another object of the invention is to provide a granular plastic materials testing apparatus in which the rate of shear can be conveniently and accurately varied in conjunction with variation in temperature so as to reflect the viscosity properties of the material.

DETAILED DESCRIPTION OF THE INVENTION

Figure 1:
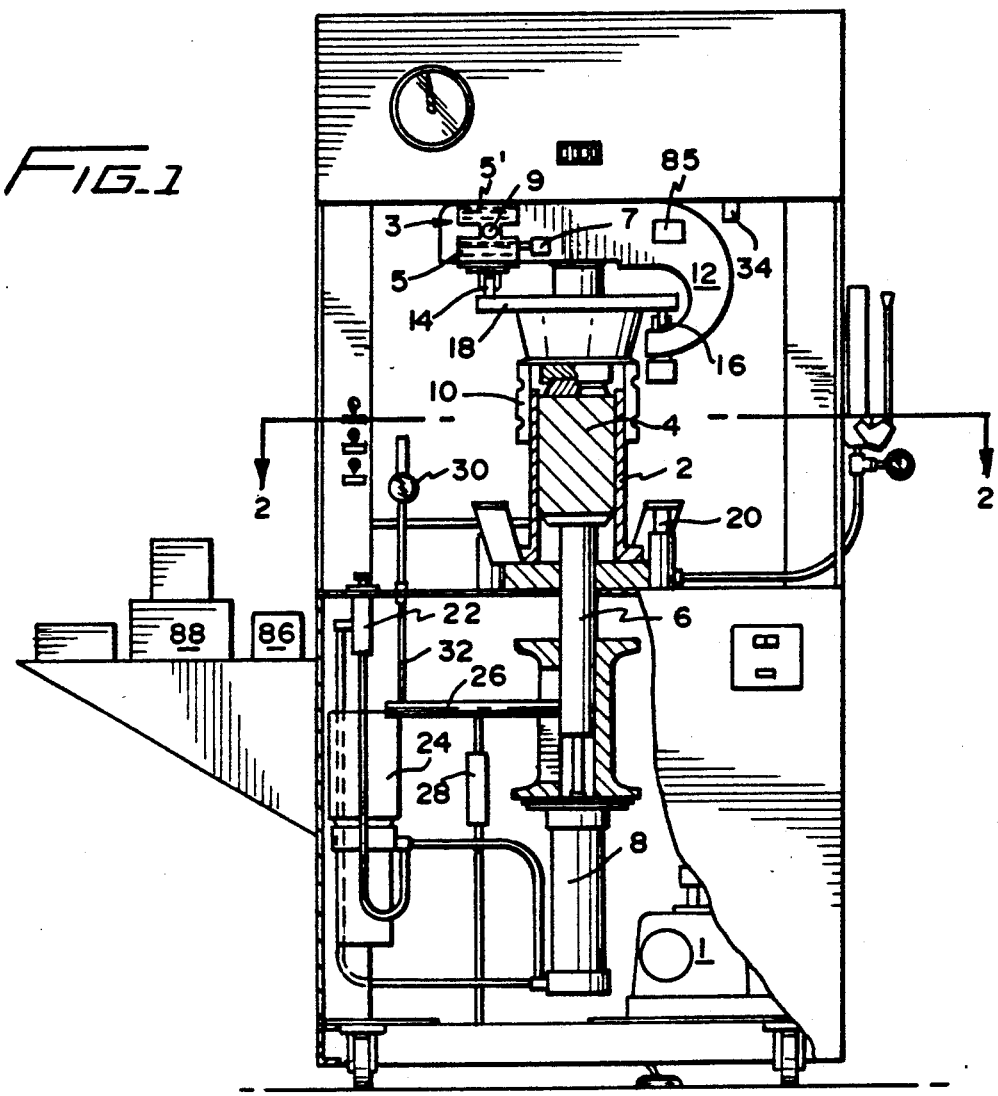
FIG. 1 is a side view in partial cross-section of an apparatus in accordance with the invention.
Figure 2:
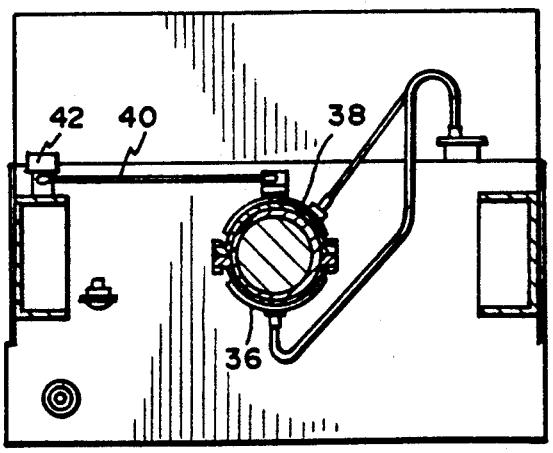
FIG. 2 is a cross-section taken along line 2—2 of FIG. 1.

Referring to FIGS. 1 and 2, pressure control valve 22 regulates hydraulic system 24 which drives cylinder 8 to move ram 6 upwardly, thus subjecting sample 4 to controlled compression loading. While sample 4 is under compression by the forces on ram 6, it is also subjected to a gyratory kneading action. A variable speed drive 1 is connected to roller carriage 12 to rotate it about a vertical axis. Rollers 14 and 16 of the carriage 12 are set at different elevations and engage flange 18 of the mold chuck 10 which engages mold 2 having sample 4 therein. The mold chuck 10 is driven in a gyratory fashion by the action of the roller carriage 12. The fixed (machine setting) gyratory angle is adjustable and is regulated by raising or lowering bottom roller 16 with respect to the roller carriage.

Figure 4:
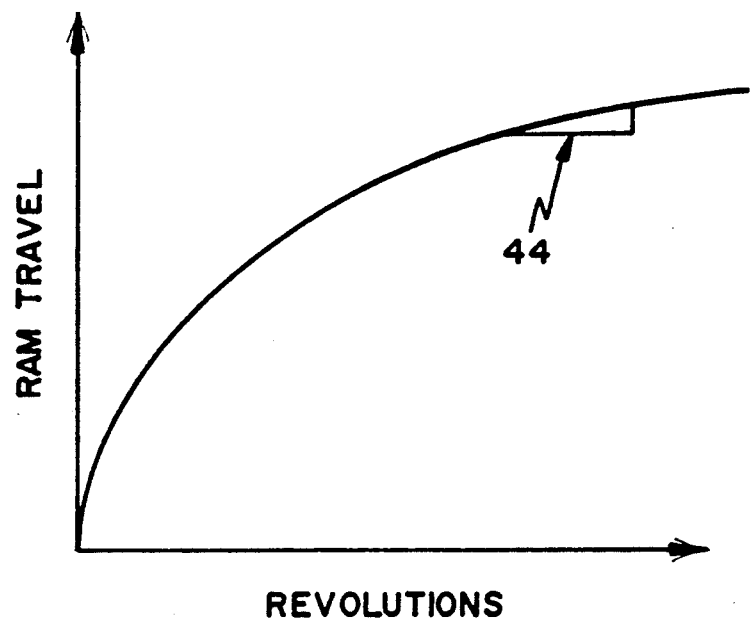
FIG. 4 is an example of a curve obtained from the machine shown in FIG. 1 indicating densification vs cycles of gyratory kneading produced by revolutions of the roller carriage.

As ram 6 moves, it carries with it a ram travel indication bar 26 which is in turn connected to ram travel transducer 28. This linear displacement transducer may be any of several known types, for example, a linear potentiometer or a linear variable differential transformer. The electronic signal produced by transducer 28 enters the circuit shown in FIG. 5 at 78 to provide an indication of compaction of the sample as illustrated by the graph of FIG. 4, which shows the relationship between densification of the sample and the number of revolutions of carriage 12. This circuitry also indicates the compression and rebound of the specimen under cyclic vertical loading, either with or without gyratory kneading.

Cyclic vertical loading is provided by control element 22. Control element 22 may be a simple valve, but preferably comprises several control valves, each of which is electronically activated. A timer (not separately shown) controls one or more solenoid relays (not separately shown) each of which is connected to a respective one of the control valves. Thus, each control valve is periodically activated by the timer to cause the ram to apply predetermined compressive forces to the sample.

This mode of loading is analogous to that which occurs in flexible pavement beneath a wheel of a moving vehicle. This is done by combining the kneading type action, caused by flexing of the structure, with cyclic vertical loading, caused by passage of the vehicle over the pavement surface. This kneading action results because the pavement deflects (like a loaded beam) as the wheel passes over the surface. While braking and accelerating also produce these actions, the primary cause is the flexing of the pavement during passage of the automobile over the pavement.

A dial gage 30 may contact travel indicating bar 26 by a shaft 32 to provide a visual indication of the travel of ram 6.

As will be appreciated more fully below, the ram travel is correlated with the number of revolutions of carriage 12 (see FIG. 4), and sensor 34, which is mounted on the machine housing, detects each revolution of carriage 12. The sensor may be any of several known types, such as magnetic or optical.

FIG. 2 is a cross-section taken along line 2—2 of FIG. 1. Adjustable front and rear heaters, 36 and 38 respectively, provide a range of selected temperatures as prescribed by the engineer. A link 40 extends outwardly from a rear face of an extension of mold chuck 10 and contacts a transducer 42 at an opposite end. Transducer 42 measures the extent of oscillation of link 40 which is proportional to the angle of gyration (gyratory angle) of mold chuck 10 containing sample 4 in mold 2. Transducer 42 may be any of several types, for example, potentiometric, capacitive or inductive, and it produces an output signal that is utilized in the circuit shown in FIG. 5 to produce a graph such as that illustrated in FIG. 3.

It will be appreciated that although the gyratory angle about the line connecting rollers 14 and 16 is fixed by the relative elevations of these rollers, mold chuck 10 is free to rotate about that line by an angle greater than that which is set by rollers 14 and 16. Thus, the magnitude of the full cycle of the gyratory angle is not set by the inclinations of the line connecting rollers 14 and 16 but is a function of the elasto-plastic properties of the sample 4 being tested.

Figure 3:
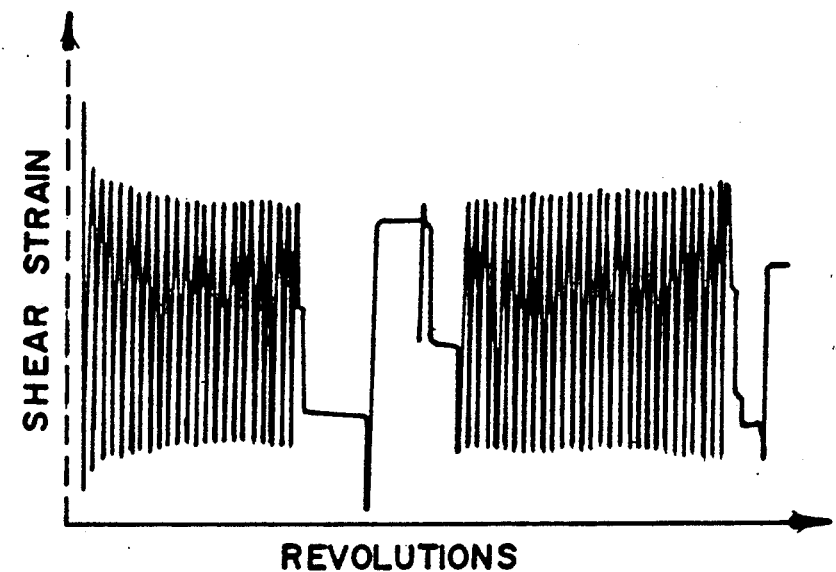
FIG. 3 is an example of a graph of shear strain vs cycles of gyratory kneading obtained from a machine such as that shown in FIG. 1.

FIG. 3 is a graphical representation of the signal from the shear strain transducer 42 as a function of the number of revolutions of carriage 12. As sample 4 (FIGS. 1 and 2) is kneaded, its plasticity, as reflected by the full cycle gyratory angle recording, reaches an intermediate minimum and then may ultimately begin to show an increase (i.e. a widening of the recording band as in FIG. 3). The beginning of progressive increase in the gyratory angle as illustrated by this recording represents a critical measurement in the design and control of the paving mixture.

FIG. 4 illustrates a critical factor in the design of paving material. As the sample is subjected to the said compressive and shear forces it becomes compacted, or densified. The degree of compaction is continuously monitored, and the point at which the compaction practically ceases to increase is important in the design of a paving material. This is illustrated in FIG. 4 by a prescribed limiting rate of densification which is set by the engineer and defined by the slope of the curve as illustrated by horizontal and vertical dimensions at 44 in FIG. 4.

Figure 5:
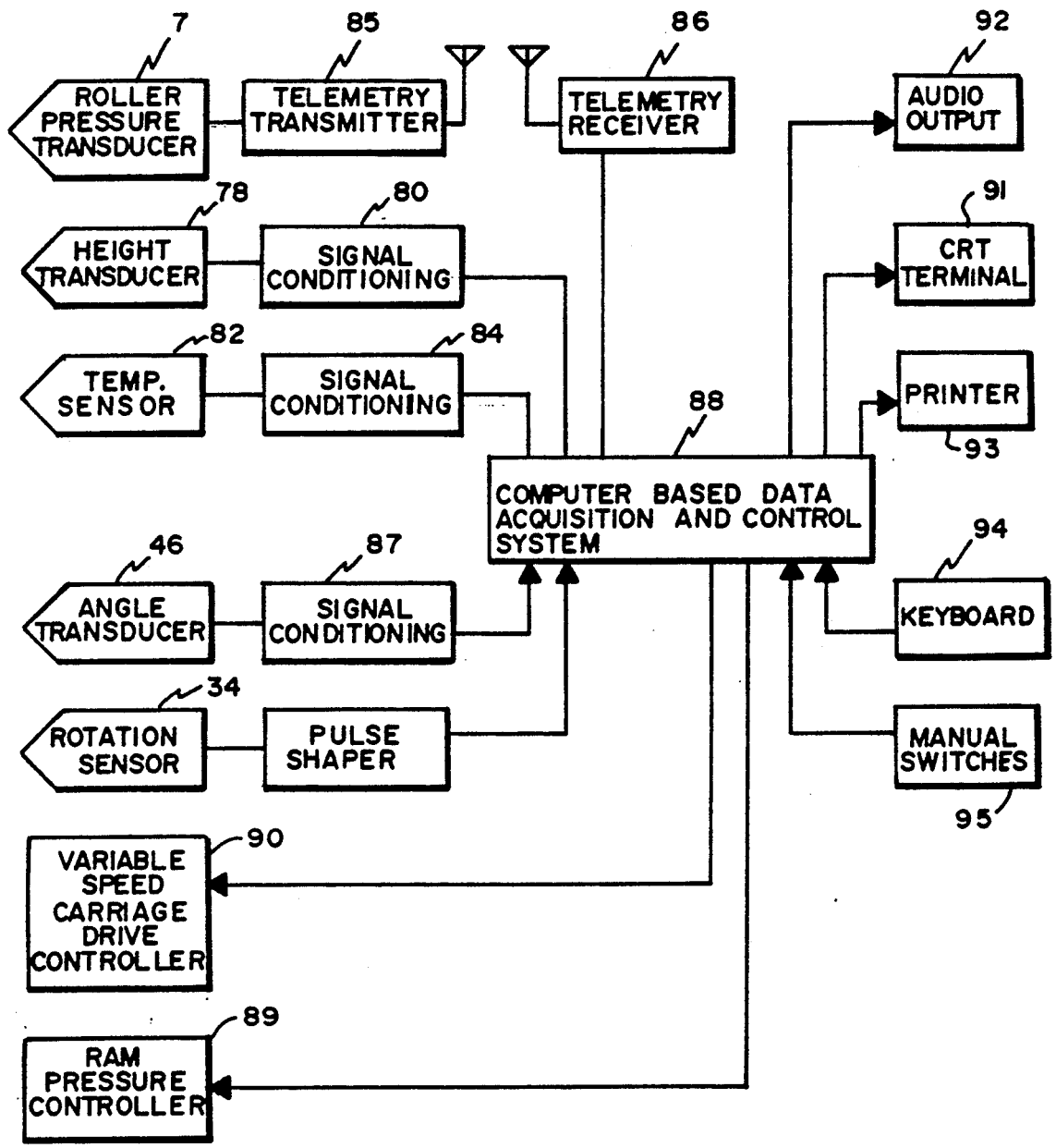
FIG. 5 is a block diagram of an electronic computer based system used with the machine shown in FIG. 1.

Referring again to FIG. 1, upper roller 14 bears on the upper surface of flange 18. Roller 14 is part of an air-oil assembly 3 which is mounted on the carriage 12. Roller 14 is supported by a shaft attached to oil cell 5 and which moves with respect to the oil cell. Force from the flange is transmitted by the roller 14 and shaft to the oil of the oil cell when roller carriage 12 rotates and deforms sample 4 in mold 2. The pressure in the oil is measured by pressure transducer 7 and indicates the shear in the sample. Assembly 3 preferably includes air cell 5' above the oil cell as shown in FIG. 1, even though it may contain only the oil cell. In either case, the pressure in the cell is converted to an electrical signal by a pressure transducer 7. The electrical signal from the roller pressure transducer 7 can be recorded on a small battery powered recorder (not shown) mounted on the roller carriage, or the signal can be transmitted to the stationary data acquisition system 88 through a telemetry system comprised of a telemetry transmitter 85 and a telemetry receiving 86 as shown in FIG. 5. The telemetry system can be any of the well known short range types using radio, optical or acoustic links between the rotating assembly and the fixed frame. This pressure-related electrical signal is used in the system shown in FIG. 5 to provide an indication of the shear occurring in the sample under the test conditions.

Upper roller assembly 14 (FIG. 1), when equipped with an air-over-oil cell, can be operated in either a fixed strain-variable stress mode (oil cell) or variable strain-variable stress mode (air-over-oil cell) by opening or closing a valve 9 which lies in a tube connecting the oil and air chambers.

A wall friction accessory 20 (FIG. 1) measures the wall friction between specimen 4 and mold 2 and is described in U.S. Pat. No. 3,478,572.

With Reference to FIG. 5, the preferred electronic system for data acquisition and control of the gyratory testing machine will be described. Electrical signals from the measuring transducers are provided as inputs to the computer based data acquisition and control system. The transducer signals are passed through appropriate signal conditioning circuits before being connected to the analog to digital converters of the computer based data acquisition system. Signals from the angle transducer 42 are received at 46 and are given additional pre-processing through a signal conditioning unit 87, that includes a peak detector circuit, before being connected to the analog to digital converter section of the data acquisition system 88. The computer based system 88 also provides output signals to control the ram pressure controller 89, the variable speed carriage drive controller 90, and to reset the peak detector circuit. The computer based system provides the operator with visual information on a CRT screen 91 and audio information through tone or simulated voice on audio channel 92. A permanent record of the test information is made on printer 93 and may be stored on a computer diskette (not shown) which is provided in the computer 88. Visual channel 91 and audio channel 92 provide means for alerting or warning the operator that preselected or critical conditions have been reached in the ongoing test. The system operator can control operation of the system through a keyboard 94 and with manually operated switches 95 which are located at strategic points on the test machine. As an alternative to the hardware circuit shown in FIG. 5, the peak-to-peak detection function can also be performed with software if a high speed computer system is used.

Figure 6:
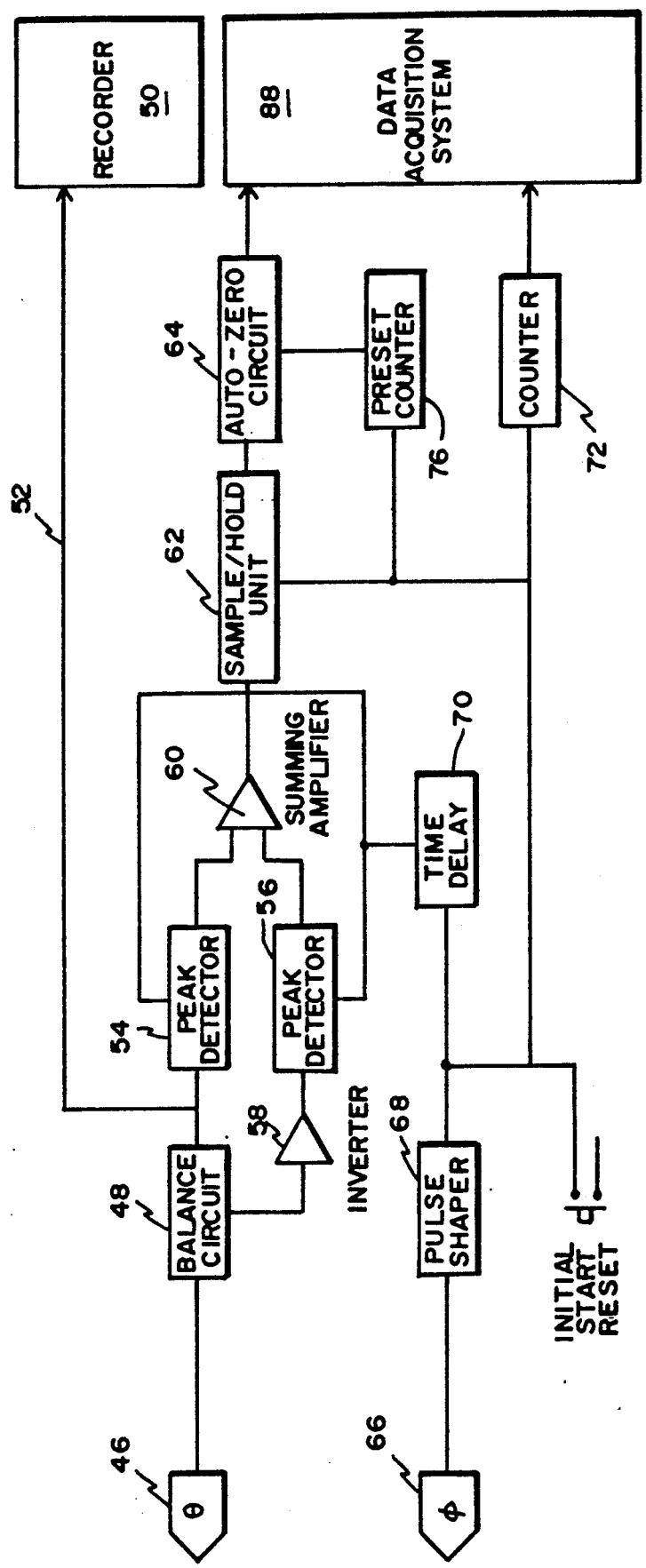
FIG. 6 is a block diagram of an electronic circuit for producing a peak-to-peak output signal from the oscillating input gyratory angle signal.

With reference to FIG. 6, the preferred circuit for preprocessing the gyratory angle signal and supplying a peak-to-peak signal to the computer will be described. Signals from transducer 42 are received at input 46, and are passed through a balance circuit 48 which removes the d.c. component. The a.c. component of this signal, which is proportional to the peak-to-peak angular change of the mold, is directed to recorder 50 directly by lead 52 and to a first peak detector 54. Peak detector 54 is commonly available and produces an output voltage which represents the maximum amplitude of the input voltage. To obtain the negative-going peak, a second peak detector 56 receives an input from balance circuit 48 after having passed through an inverter 58. The voltage outputs from peak detectors 54 and 56 are added at summing amplifier 60 to electronically determine the peak-to-peak excursion of the signal from transducer 42 which in turn represents the peak-to-peak gyratory angle of mold chuck 10. The output of the summing amplifier is passed through a sample and hold unit 62 and an auto-zero circuit 64 which eliminates d.c. component of the signal before being applied to strip chart recorder 50 or the computer based data acquisition system 88.

Signals from revolution sensor 34 are applied at input 66 and are in turn fed to a pulse shaper 68 to form them into rectangular pulses. Time delay circuit 70 accepts revolution pulses from pulse shaper 68 and supplies reset pulses to the digital control inputs to peak detectors 54 and 56. The control pulse timing is adjusted so that the peak detectors hold the positive and negative peak angle signals for slightly over half of each revolution and until the sample/hold unit acquires the summing amplifier output. Pulses from the pulse shaper circuit determine the timing of the sample/hold action with respect to carriage rotation position. The time delay circuit 70 also accepts a pulse from the pulse shaper and then outputs a pulse to the control inputs of the peak detectors. The timing of the reset pulse going to the peak detector is adjusted to lag behind the sample/hold action until that circuit is fully settled. The pulses from pulse shaper 68 are also counted by the counter 72 to indicate the number of revolutions of carriage 12. A reset switch 74 sets the beginning condition. A preset counter 76 controls the auto-zero circuit by allowing several cycles to be accumulated before operation of the auto-zero circuitry 64. The pulse timing and counting function can also be performed using software if a high speed computer is used with system.

With reference to FIG. 5, signals from ram travel transducer 28 are applied at input 78 and pass through a balance circuit 80 after which they are recorded on a strip chart recorder or in the computer based data acquisition system 88.

With reference to FIG. 2, a front heater 36 and a back heater 38, coupled with a thermostat, provide a prescribed temperature control for the sample 4. Electronic signals from a temperature transducer (not shown), located in the sample mold, are applied to the circuit of FIG. 5 at input 82 and are passed through a signal conditioner 84 and then to a separate recorder or to the computer based data acquisition system shown in FIG. 5.

In operation, a sample to be tested is placed in the mold and the machine is activated. The ram is pushed upward into the mold to compress the sample, and the carriage 12 rotates to subject the sample to kneading. Signals from the various sensors are supplied to the data acquisition system to monitor the compaction and the number of gyratory cycles. The audio and visual terminals provide continuous displays for the operator to monitor the testing. These displays show when the peak-to-peak gyratory angle reaches a minimum and also when it reaches a maximum. This function is automatically determined by the circuitry shown in FIG. 6. The gyratory angle (peak-to-peak) thus measured is a direct measure of shear strain in the material being tested. Both the minimum and maximum values of gyratory angle are used in calculating the predicted performance of the material being tested. The operator may choose values for any of the variable factors by use of keyboard input 94, and decides whether the roller carriage is to be driven by a fixed pressure on the rollers or by a variable pressure by opening or closing the valve 9 in the air-oil assembly 3.

It will be appreciated that a novel improved testing machine has been described for measuring fundamental pavement material (subgrade, base and pavement) design parameters, and for collecting, processing and displaying said parameters in such fashion as to demonstrate important basic interrelationships in a manner that makes possible a rational approach to pavement mixture design testing, which has heretofore not been available to the engineer. Modifications within the scope of the appended claims will be apparent t those having skill in the art.

I claim:

1. In a materials measuring machine of the type having a mold chuck mounted for gyratory oscillation for subjecting a sample to controlled shear strain and for controlling shear stress, the improvement comprising means for continuously measuring and indicating changes in the density of said sample.

2. A machine according to claim 1 wherein said means for continuously measuring and indicating changes in the density of said sample comprises means for determining when the rate of change of the density indicates a prescribed rate of densification of said sample.

3. A machine according to claim 2 wherein said means for continuously measuring and indicating changes in the density of said sample comprise a ram for compacting said sample and a transducer for indicating the travel of said ram.

4. A machine according to claim 3 wherein said means for continuously measuring and indicating changes in the density of said sample further comprises an electronic circuit for receiving data from said transducer and for recording said data.

* * * * *